US011262351B2

(12) United States Patent
Dafforn et al.

(10) Patent No.: US 11,262,351 B2
(45) Date of Patent: Mar. 1, 2022

(54) APPARATUS AND METHOD FOR IMPROVED MOLECULAR DETECTION

(71) Applicant: The University of Birmingham, Birmingham (GB)

(72) Inventors: Timothy Dafforn, Warwickshire (GB); Matthew Hicks, West Midlands (GB)

(73) Assignee: The University of Birmingham, Birmingham (GB)

( * ) Notice: Subject to any disclaimer, the term of this patent is extended or adjusted under 35 U.S.C. 154(b) by 402 days.

(21) Appl. No.: 15/759,760

(22) PCT Filed: Sep. 16, 2016

(86) PCT No.: PCT/GB2016/052890
§ 371 (c)(1),
(2) Date: Mar. 13, 2018

(87) PCT Pub. No.: WO2017/046597
PCT Pub. Date: Mar. 23, 2017

(65) Prior Publication Data
US 2018/0180603 A1    Jun. 28, 2018

(30) Foreign Application Priority Data
Sep. 18, 2015 (GB) ...................... 1516568

(51) Int. Cl.
*G01N 33/542* (2006.01)
*G01N 21/19* (2006.01)
(Continued)

(52) U.S. Cl.
CPC .......... *G01N 33/542* (2013.01); *G01N 21/19* (2013.01); *G01N 33/54373* (2013.01); *C12Q 1/6816* (2013.01); *G01N 2201/061* (2013.01)

(58) Field of Classification Search
CPC ................. G01N 33/542; G01N 21/19; G01N 33/54373; G01N 2470/12; C12Q 1/6816
(Continued)

(56) References Cited

U.S. PATENT DOCUMENTS

2010/0053619 A1    3/2010   Dafforn

FOREIGN PATENT DOCUMENTS

| WO | 2012/001521 A2 | 1/2012 |
| WO | 2015/181546 A1 | 12/2015 |
| WO | 2015/181547 A1 | 12/2015 |

OTHER PUBLICATIONS

Sandhu (2014) "Development of a biosensor based on linear dichroism spectroscopy" Thesis submitted to Univ of Birmingham. (Year: 2014).*
(Continued)

*Primary Examiner* — Christopher L Chin
(74) *Attorney, Agent, or Firm* — Brooks Kushman P.C.

(57) ABSTRACT

Provided is a method that utilises linear dichroism (LD) to identify the presence of a target molecule (L) in a sample. The method comprises providing an alignable scaffold (20), preferably biomolecular fibre M13, comprising a first binding region and having a high aspect ratio of greater than 5:1, providing a substrate (e.g. a substantially spherical non-alignable moiety (12)) comprising a second binding region which binds the first binding region in the absence of the target molecule in such a way that the LD signal of the alignable scaffold is reduced or minimised relative to the unbound and aligned scaffold, wherein one of the first and second binding regions is a receptor capable of binding the target molecule, exposing the substrate-bound scaffold to the sample such that binding of the target molecule, if present, to the receptor releases the scaffold from the substrate, and measuring the LD signal of the scaffold before and after exposure to the sample. A reagent and an apparatus for use
(Continued)

Figure 1A:
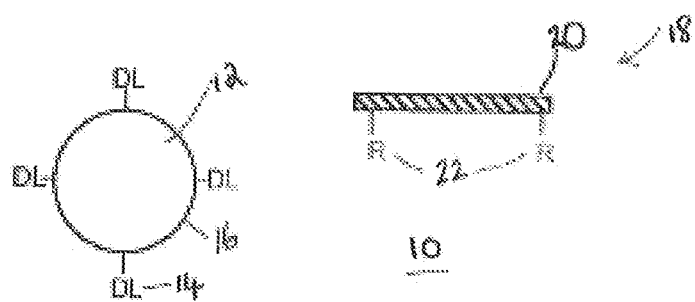

in the method are also provided. A reagent (10) and an apparatus for use in the method are also disclosed.

18 Claims, 3 Drawing Sheets

(51) Int. Cl.
   *G01N 33/543* (2006.01)
   *C12Q 1/6816* (2018.01)
(58) Field of Classification Search
   USPC ............. 422/82.05, 82.08, 82.11; 435/288.7; 436/537, 805; 356/935; 977/742
   See application file for complete search history.

(56) References Cited

OTHER PUBLICATIONS

Sandeep Kaur Sandhu, et al.: "Development of a biosensor based on linear dichroism spectroscopy", Nov. 10, 2016, Retrieved from the internet.
Lijuan Tang, et al: "Chirality-based Au@Ag Nanorod Dimers Sensor for Ultrasensitive PSA Detection", ACS Applied Materials and Interfaces, vol. 7, No. 23. May 27, 2015, pp. 12708-12712.
James Carr-Smith, et al.: "Polymerase Chain Reaction on a Viral Nanoparticle", ACS Synthetic Biology, vol. 4, No. 12, Jun. 5, 2015, pp. 1316-1325.
Donatien Ramiandrisoa, et al.: "Optical protein detection based on magnetic clusters rotation", New Biotechnology, vol. 32, No. 5. Apr. 4, 2015, pp. 467-472.
Goldman E R, et al.: "A Hybrid Quantum Dot-Antibody Fragment Florescence Resonance Energy Transfer-Based TNT Sensor", Journal of the American Chemical Society, American Chemical Society, US, vol. 127, No. 18, Apr. 13, 2005, pp. 6744-6751.
Raul Pacheco-Gomez, et al.: "Detection of Pathogenic Bacteria Using a Homogeneous Immunoassay Based on Shear Alignment of Virus Particles and Linear Dichroism", Analytical Chemistry, vol. 84, No. 1, Oct. 24, 2011, pp. 91-97.
Ju Hun Lee, et al.: "Amplified Protein Detection and Identification through DNA-Conjugated M13 Bacteriophage", ACS NANO, vol. 6, No. 6, May 15, 2012, pp. 5621-5626.
Jascindra Rajendra, et al.,: "The Binding of Single-Stranded DNA and PNA to Single-Walled Carbon Nanotubes Probed by Flow Linear Dichroism", Chemistry—A European Journal, vol. 11, No. 16, Jun. 14, 2005, pp. 4841-4847.
British Search Report dated Feb. 17, 2016 in connection with British Patent Appl. No. GB1516568.1.
PCT Search Report dated Nov. 23, 2016 in connection with PCT/GB2016/052890.
IPER issued Mar. 29, 2018 in connection with PCT/GB2016/052890.

* cited by examiner

APPARATUS AND METHOD FOR IMPROVED MOLECULAR DETECTION

FIELD OF THE INVENTION

This invention relates to a method that utilises linear dichroism to identify the presence of a target molecule in a sample, particularly a small target molecule. The invention also relates to a reagent and an apparatus for use in the method.

BACKGROUND TO THE INVENTION

By their nature, organisms contain many complex molecules and molecular assemblies. Some of the most important molecules and assemblies are large and have high aspect ratios (i.e. one axis significantly greater in length than any other). It is known to use an optical apparatus to specifically detect these high aspect ratio molecules. Such an apparatus relies on the way these long molecules interact with polarised light (i.e. light with an electric field established in one direction only).

The phenomenon being exploited in the above apparatus is known as dichroism. The incident light may be either linearly polarised, giving rise to linear dichroism (LD), or circularly polarised, giving rise to circular dichroism (CD). LD is the property exhibited by some molecular structures whereby linearly polarised light is differentially absorbed along two orthogonal axes. CD relates to the difference in absorption of left and right circularly polarised light. A molecule that is capable of selective light absorption is known as a chromophore. Dichroic molecules, i.e. those that exhibit dichroic properties, are a particular type of chromophore. Examples of dichroic materials are certain natural crystals, stretched polymers, and other non-isotropic molecules. Biomolecules contain a wide range of chromophores (including aromatic side chains, nucleotides and peptide backbones).

In order to be able to observe a dichroic effect, it is necessary that the chromophores be aligned, or at least partially aligned, with respect to the incident polarised light beams. This requirement has the advantage of allowing the extraction of data only from aligned molecules in a milieu of unaligned molecules. However, this requirement has also limited the application of the above technique, primarily, to the study of large molecules with high aspect ratios, since these are easily alignable. A molecule is considered to have a high aspect ratio if one axis is substantially longer than the other. Suitable molecules may be in the shape of a rod, a disc or a cruciform. Depending upon the stiffness of the molecule, an aspect ratio of 100:1 may be sufficient to facilitate alignment but an aspect ratio of greater than 1000:1 is preferable. Some examples of moieties of interest that have been successfully aligned include linear biomolecules in the form of DNA, fibrous proteins and membranes (including membrane proteins) (Marrington R, Small E, Rodger A, Dafforn T R, Addinall S G, "FtsZ fiber bundling is triggered by a conformational change in bound GTP" J Biol Chem 2004; 279(47):48821-48829; Dafforn T R, Rajendra J, Halsall D J, Serpell L C, Rodger A, "Protein fiber linear dichroism for structure determination and kinetics in a low-volume, low-wavelength couette flow cell" Biophys J 2004; 86(1 Pt 1):404-410; Dafforn T R, Rodger A, "Linear dichroism of biomolecules: which way is up?" Curr Opin Struct Biol 2004; 14(5):541-546; Halsall D J, Rodger A, Dafforn T R, "Linear dichroism for the detection of single base pair mutations" Chem Commun (Camb) 2001(23): 2410-2411).

A particularly convenient method for aligning such molecules is to create a solution including the molecules and then to flow the solution. Due to the elongate nature of the molecules, alignment arises as a result of shear forces generated by the flow, making the sample suitable for exhibiting the effect of linear dichroism.

In a known apparatus, once the molecules of interest have been aligned, linearly polarised light is directed through the solution from a direction substantially perpendicular to the axes of the aligned molecules. Absorption of light occurs within a molecule because, at a particular wavelength, the electric field of radiation urges the electrons in the molecule in a particular direction. When several molecules are similarly aligned, the electrons in each are all characterised by the same preferred net displacement direction. LD is a measure of the difference of absorbance of the incident light between two orthogonal polarisations. Varying the wavelength of the incident light and detecting the light emerging from the sample, allows a spectrum to be obtained which illustrates the absorbance of the sample with respect to wavelength.

An LD spectrum of a molecule provides information on the chromophores that are present including the orientation of the chromophores (and hence molecular conformation) and the orientation of the chromophores with respect to the axes of polarization. This information is important in understanding the structure of the molecule. Note that LD is a measurement of a sample's bulk property. The strength of the absorbance can be used to quantify the number of target molecules that are present in the sample. In addition, since LD is extremely sensitive to changes in alignment, an anomaly in the structure of a molecule may be detected. For example, LD can detect the distortion caused by a single mismatched hydrogen bond in a 1300 bp (base pair) fragment of DNA.

Furthermore, LD is extremely sensitive to the formation of a complex since the binding of an aligned molecule to a second molecule has the following two measurable effects.
1) The shape of the aligning moiety is altered and this results in its alignment also being altered, which leads to a change in the observed LD spectrum.
2) The second molecule itself becomes aligned by virtue of its attachment to the aligned molecule. This leads to the generation of an LD signal for the previously unaligned chromophores of the second molecule. Thus, information on the structure of the complex can be obtained.

Both of the above effects result in detectable phenomena that can be used to detect the formation of complexes. Not only can structural information be gleaned regarding the nature of the complex but the affinity of the interaction can also be determined.

WO 2008/059280 discloses a molecular sensor in which the sensor element comprised a scaffold moiety with a high aspect ratio having a receptor moiety attached thereto. The use of an alignable scaffold moiety for the attachment of a receptor moiety meant that neither the receptor moiety itself nor the target molecule required inherent alignment properties. As well as being able to identify the aligned molecules through the resulting dichroic spectrum, the sensor can be used to quantify the aligned molecules and to detect the presence of molecular anomalies such as mismatches. The binding properties of the receptor moiety and target molecule may also be studied using the sensor. The inherent nature of dichroic molecules means that the sensor is extremely sensitive.

This system, although useful in many instances, has a number of practical limitations. Firstly, the target molecule needs to be large enough to significantly alter the alignment of the alignable scaffold upon binding to the receptor moiety, in order for a change in LD signal to be detected. This limits the application of the system to detection and analysis of target molecules which are of similar magnitude or greater than the size of the alignable scaffold. The second limitation of the system is that the signal that is produced by binding between the alignable scaffold and the target molecule is a decrease in signal. Within the diagnostics industry it is seen to be advantageous that an assay signal increases when a target is present.

The present invention represents a further development of the system disclosed in WO 2008/059280, providing an assay that can be used to detect smaller targets resulting in an increase of LD signal upon detection.

SUMMARY OF THE INVENTION

A method for detecting the presence of a target molecule in a sample, comprising the steps of:
providing an alignable scaffold comprising a first binding region and having a high aspect ratio;
providing a substrate comprising a second binding region which binds the first binding region in the absence of the target molecule in such a way that the LD signal of the alignable scaffold is reduced or minimised relative to the unbound and aligned scaffold, wherein one of the first and second binding regions is a receptor capable of binding the target molecule;
exposing the substrate-bound scaffold to the sample such that binding of the target molecule, if present, to the receptor releases the scaffold from the substrate; and
measuring the LD signal of the scaffold before and after exposure to the sample with an LD spectrometer.

An increase in the LD signal of the scaffold after exposure of the substrate-bound scaffold to the sample is indicative of the presence of the target molecule in the sample.

It will be understood that in some embodiments the receptor may be the first binding region. In those embodiments, the receptor may be an integral part of the scaffold or alternatively the method may include a step of attaching a receptor to the scaffold to form a receptor/scaffold complex. Similarly, the second binding region may form an integral part of the substrate, or alternatively the method may include a step of modifying the substrate by attachment of a moiety containing/constituting the second binding region. Upon exposure to the target molecule a complex is formed between the scaffold/receptor and target molecule. The above applies mutatis mutandis to embodiments where the receptor is the second binding region. In those embodiments, the target molecule becomes bound to the substrate (via the receptor).

The method of the invention thus enables an increase in the LD signal of the scaffold to be detected upon binding of the target molecule to the receptor. In the absence of the target molecule, the scaffold is bound or sequestered by the substrate so as to minimise or reduce the LD signal of the scaffold. In the presence of the target molecule, the scaffold is released from the substrate and is allowed to align, thereby resulting in an increased LD signal. Advantageously, because the degree of increase in the LD signal is not dependent on the size of the target molecule, but is instead dependent on the binding and release of the scaffold by the substrate, the method is particularly useful for detecting small target molecules which are not themselves able to effect a significant change in the alignment of the scaffold.

Methods for detecting the LD signal of the scaffold will be known to those skilled in the art. The LD signal can be measured by inducing alignment of the scaffold in solution, for example by providing a flow path. The flow path may be conveniently provided by a Couette cell. Other methods for alignment include shear flow, magnetic alignment or use of squeezed gels. Polarised light is then passed through the flow path, and is detected after it has passed through the flow path.

The scaffold moiety may be any material which is alignable under flow conditions (at least when the first binding region is incorporated). In order to be alignable, the scaffold moiety must have a high aspect ratio. As used herein a high aspect ratio relates to an aspect ratio greater than 5:1, 20:1, 50:1, 75:1 and in some embodiments greater than 100:1.

Examples of suitable scaffold moieties (which may subsequently be modified to include the first binding region) include synthetic and natural polymers, carbon nanotubes and biomolecular fibres. As used herein a biomolecular fibre is any biomolecule having the required high aspect ratio and which is alignable under flow conditions. Examples of biomolecular fibres include lipid vesicles, filamentous bacteriophage and polymers such as amino acid polymers (i.e. polypeptides or proteins), and nucleic acid polymers (i.e. RNA or DNA). In some embodiments, the biomolecular fibre is a filamentous bacteriophage, such as M13, f1, fd, Ike, N1 or a peptide nucleic acid (PNA).

In some embodiments the modified scaffold moiety exhibits dichroism in the visible spectrum.

The scaffold moiety may comprise two or more distinct first binding regions.

In an embodiment, the first binding region is a receptor for the target molecule and the substrate comprises one or more second binding regions which comprises at least a portion of the target molecule. In a further embodiment, the second binding region consists of the target molecule.

The second binding region may be in the form of a ligand. The ligand may be attached to the substrate by covalent interactions. A strong covalent interaction or linkage between the ligand and the substrate prevents "leaching" or detachment of the ligand from the substrate. Alternatively, the ligand may be attached to the substrate by non-covalent interactions.

The ligand(s) may be attached to the substrate via amine, carboxylic acid, sulfhydryl, phosphate or other reactive groups on the ligands to reactive groups on the substrate. This could be carried out for example by the use of homo/hetero bi-functional cross-linkers which are readily available. Suitable crosslinkers include those using maleimide and succinimide groups. Other approaches could include the use of strong non-covalent interactions for example between streptavidin and biotin (one on the substrate and one on the ligand).

Thus the interaction between the second binding region (ligand) of the substrate and the first binding region of the scaffold in the absence of free target molecules in the sample, minimises or reduces the LD signal of the scaffold. When the substrate-bound scaffold is exposed to the sample, any free target molecules present in the sample compete for the receptor. Binding of the free target molecule to the receptor (whether that be part of the scaffold or substrate) releases the scaffold from the substrate, allowing it to become aligned. Of course it will be understood that in this context alignment of the scaffold may refer to a scaffold/receptor complex bound to the target molecule or merely the scaffold and its associated binding region (in the latter case the target molecule being bound to the substrate/receptor complex).

In an embodiment, the increase in the LD signal detected is proportional to the concentration of the target molecules in the sample. In this embodiment, the free target molecules and relevant binding region bind to the receptor via non-covalent interactions, so that competition for the receptor between the target molecules and the relevant binding region creates a chemical equilibrium.

In an embodiment, the substrate binds the scaffold such that the LD signal of the bound scaffold is substantially zero.

In a first series of embodiments, the substrate binds the scaffold such that the scaffold is in a non-aligned form (i.e. it is prevented from aligning by the substrate), thereby minimising or reducing the LD signal of the scaffold. The substrate may comprise or consist of a non-alignable moiety (NAM).

The NAM may be any species which exhibits low alignment under the conditions applied to the reaction vessel. This ensures that the non-alignable moiety has a small LD signal and, therefore, that the NAM-bound scaffold also has a small LD signal. In an embodiment, the NAM is substantially spherical. Spherical objects cannot align and so have very low LD signals. Examples of suitable NAMs include beads (e.g. agarose or sepharose beads), magnetic iron or other metal particles.

In an alternative series of embodiments, the substrate may comprise or consist of an alignable moiety which is only rendered unalignable by virtue of it being bound to the scaffold. In some embodiments, the scaffold moiety and substrate may be substantially the same.

A NAM that is dissolved in solution (or suspended) must have spectral properties such that it does not significantly disturb the LD signal of the alignable scaffold. This means that the NAM should not absorb, fluoresce or phosphoresce in the region of the spectrum of the LD signal of the alignable scaffold.

In those embodiments where the LD signal is measured by inducing alignment of the scaffold in solution, the substrate may alternatively comprise or consist of a surface within a reaction vessel. One or more ligands may be attached to the surface which bind to the first binding region of the scaffold, thereby sequestering the scaffold to the surface in a non-alignable form.

Figure 6:
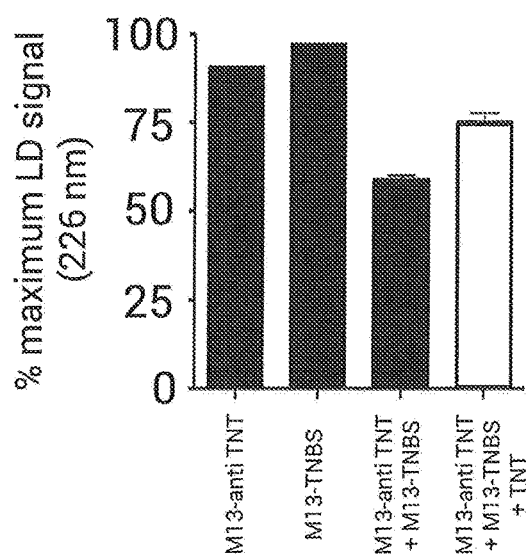

In a second series of embodiments, the substrate binds the scaffold so that the scaffold is held outside of the beam of polarised light of the LD spectrometer. The substrate may be a surface which itself is outside of the beam of the LD spectrometer. The substrate may be a surface of a reaction vessel. In this embodiment, release of the scaffold in the presence of free target molecules allows the alignable scaffold to move into the beam, allowing an LD signal to be recorded.

The affinity between the substrate (either a non-alignable moiety or a surface) and the ligand(s) must be greater than the affinity between the receptor moiety and the target molecule. In an embodiment, the affinity between the non-alignable moiety or surface and the ligand(s) is significantly greater than the affinity between the receptor moiety and the target molecule.

Ideally, the target molecule is significantly smaller in size than the alignable scaffold such that upon binding to the receptor moiety of the scaffold/receptor complex, the target does not cause a reduction in the alignment of the scaffold and hence a decrease in the LD signal of the alignable scaffold. The target molecule may be less than 40%, less than 25% or less than 10% of the size of the scaffold.

[According to a second aspect of the present invention, there is provided a reagent for use in the method of the first aspect of the invention, the reagent comprising:

an alignable scaffold comprising a first binding region and having a high aspect ratio; and a substrate comprising a second binding region, wherein one of the first and second binding regions is a receptor capable of binding a target molecule; and wherein in the absence of the target molecule, the substrate and scaffold are bound via their respective binding regions in such a way that the scaffold is not aligned.

According to a third aspect of the present invention, there is provided an apparatus for use in the method of the first aspect of the invention, the apparatus comprising:

a source of polarised light;

a reaction vessel comprising a surface adapted to bind a binding region of an alignable scaffold;

means for applying an alignment potential to a sample potentially containing a target molecule and a detector arranged to receive light from the source after it has passed through the sample;

wherein a light path is defined between the light source and the detector. Reference to "means for applying an alignment potential" encompasses all known mechanisms for creating alignment whereby linear dichroism may be observed.

Examples include but are not limited to the use of flow cells, Couette cells, magnetic alignment or squeezed gels.

In an embodiment, the surface may be arranged such that, in use, it is outside of the light path. In an alternative embodiment, the surface is configured to bind the scaffold in a non-alignable form. For example the scaffold may be provided with an antibody specific for an antigen (e.g. collagen) that covers the surface of the substrate.

It will be understood that embodiments described above in relation to the first aspect of the invention may also relate to the second and third aspects of the invention.

BRIEF DESCRIPTION OF THE DRAWINGS

Embodiments of the invention will now be described by way of example with reference to the accompanying drawings in which:

FIG. 1*a* is a schematic of a non-alignable moiety with attached ligands, prior to binding a scaffold/receptor complex, in accordance with an embodiment of the present invention;

FIG. 1*b* is a schematic showing the release of a scaffold/receptor complex from the non-alignable moiety of FIG. 1*a*, in the presence of free target molecules;

FIG. 2 is a schematic showing the release of a scaffold/receptor complex from a surface derivatised with ligands in the presence of free target molecules, in accordance with an alternative embodiment of the present invention;

FIG. 3 is a UV/Vis spectra of 0.07 mg/mL M13 conjugated with anti-FITC (M13+anti-Fluorescein) and 0.08 mg/mL M13 conjugated with FITC (M13+FITC), FIG. 4 is LD spectra for embodiments of the invention, FIG. 5 is a bar chart showing the LD spectra for solution containing varying concentrations of fluorescein as target molecule, and FIG. 6 is an example of the detection of the explosive trinitrotoluene (TNT).

DETAILED DESCRIPTION OF CERTAIN EMBODIMENTS

Referring to FIG. 1a, a reagent 10 for detecting the presence of a target molecule in a sample using linear dichroism comprises a substrate in the form of a substantially spherical non-alignable moiety 12 having a plurality of dummy ligands (DL) 14 attached to its surface 16. The reagent 10 further comprises an alignable scaffold/receptor complex 18 comprising a scaffold moiety 20 to which is attached receptor moieties 22. The receptors 22 are specific for a target molecule (ligand L, not shown).

Figure 1B:
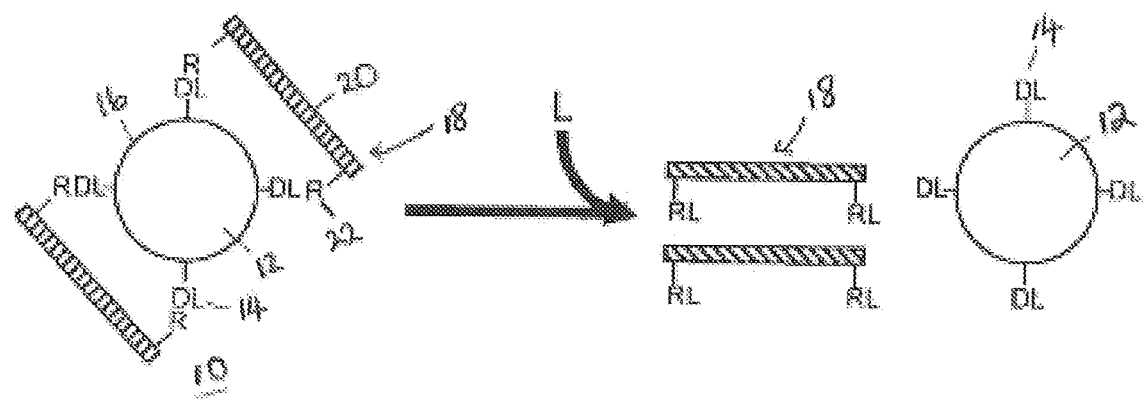

As shown in FIG. 1b, in the absence of the target molecule (ligand L), the receptor moieties 22 bind to the dummy ligands 14 on the surface 16 of the non-alignable moiety 12, thereby sequestering the scaffold/receptor complexes 18 in a non-alignable form. The NAM-bound scaffold/receptor complexes 18 have a much reduced LD signal compared to the free aligned scaffold/receptor complexes. As such, the LD signal of the scaffold/receptor complex 18 in the absence of the target molecule L is minimised. When the reagent 10 is exposed to a sample containing the free target molecule L, the free target molecule L competes with the dummy ligands 14 on the NAM 12 for the receptor binding sites 22 on the alignable scaffold 20. This leads to a release of the scaffold/receptor complexes 18 (with the receptor-bound target molecule L) from the NAM 12, allowing them to become aligned and resulting in an increase in the LD signal.

Figure 2:
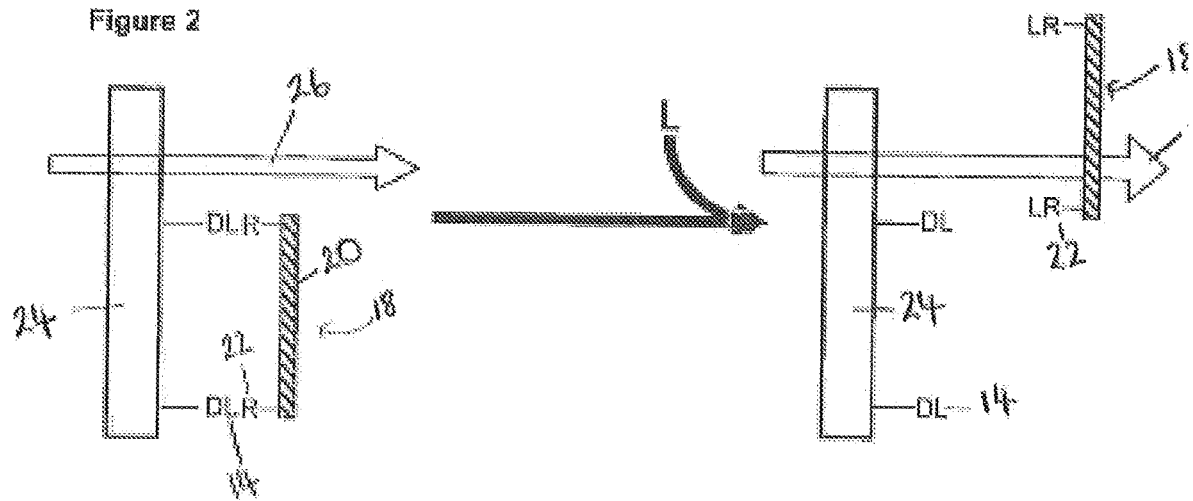

In an alternative embodiment, shown in FIG. 2, the substrate takes the form of a surface 24 to which is attached a number of attached dummy ligands 14. The dummy ligands 14 bind to the receptors 22 so that the scaffold/receptor complex 18 is held outside of the polarised light beam 26 of the LD spectrometer, so that the observed LD signal is zero. Upon addition of the free target molecule L, the scaffold/receptor complex 18 is released from the surface 24 by the competitive binding of the target molecule L to the receptors 22, displacing the dummy ligands 14 from the binding sites of the receptors 22. The released scaffold/receptor complex 18 (with the bound target molecules L) is then free to move into the beam 26 of the LD spectrometer, allowing an LD signal to be recorded.

Example 1

The M13 bacteriophage aggregation assay behaves like a competition assay. It consists of M13 conjugated with target antigens which form a complex with anti-target antibody labelled M13. This complex reduces the LD signal. The addition of an unknown quantity of target molecules will compete with the target antigens conjugated on to the M13 for the binding sites on the M13 bacteriophages. A dissociation of conjugated M13 from the complex allows the preferential alignment of both the M13 bacteriophages. This results in the appearance of an LD signal, thus signifying the presence of the target molecule in the sample.

The target molecule chosen for detection was Fluorescein isothiocyanate (FITC). FITC was covalently linked to the free amine groups (one on the N-terminus and one on the lysine residue) on the p8 coat protein by forming an amide bond. A second reagent was then constructed that contained the anti-fluorescein antibody covalently attached to the p8 co-protein on a second M13 bacteriophage In order to conjugate M13 with anti-FITC, M13 had to be modified with SATA and anti-FITC had to be modified with SMCC. The SATA attached sulfhydryl groups on to free amine groups on the p8 coat protein. SMCC attached maleimide groups on to the Ab and the maleimide groups were able to react with the sulfhydryl groups on the M13 to form thioether bonds.

Increasing concentrations of fluorescein (0.01 mM, 0.02 mM, 0.04 mM, 0.1 mM, 0.2 mM, 0.5 mM, 1 mM and 2 mM) were added to M13 conjugated with anti-fluorescein and left to incubate overnight. M13 conjugated with fluorescein was added to the solution, after which the LD signal was measured to indicate if increasing concentrations of fluorescein were able to compete with the fluorescein on the M13 to bind with the anti-fluorescein Abs. These signals were compared to the control which consisted of M13 conjugated with anti-fluorescein and M13 conjugated with fluorescein and contained no fluorescein. Another control was designed where 0.02 mM rhodamine was added to the assay to determine the specificity of the assay.

Detection of Fluorescein Using LD and Anti-Fluorescein and Fluorescein Labelled M13

The reagents required for the detection of fluorescein in this assay included M13 conjugated with anti-fluorescein and M13 conjugated with fluorescein. The UV/Ms absorbance spectrum was measured to determine the concentration.

Figure 3:
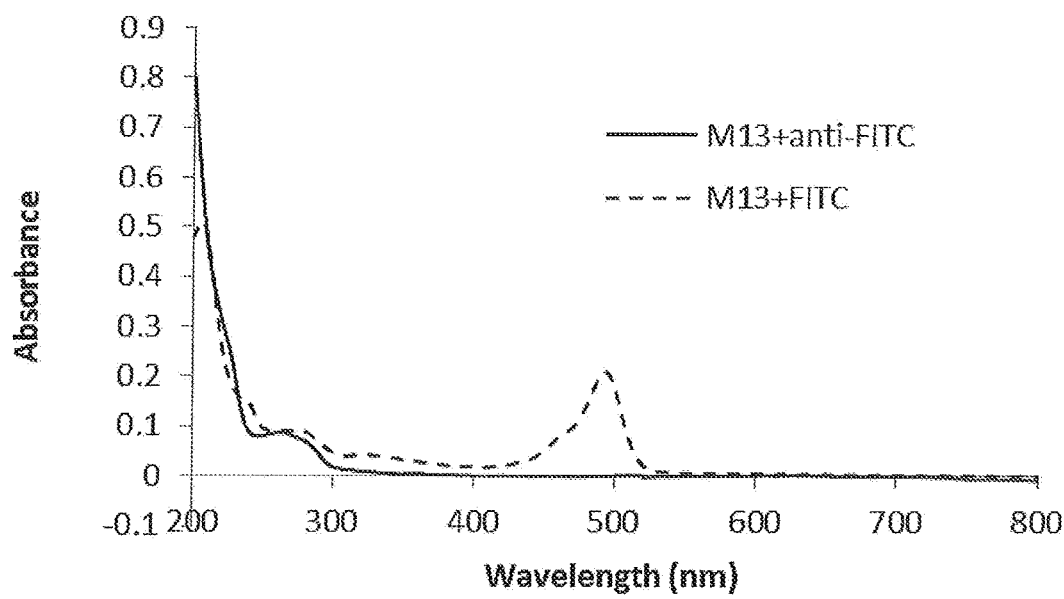
Figure 4:
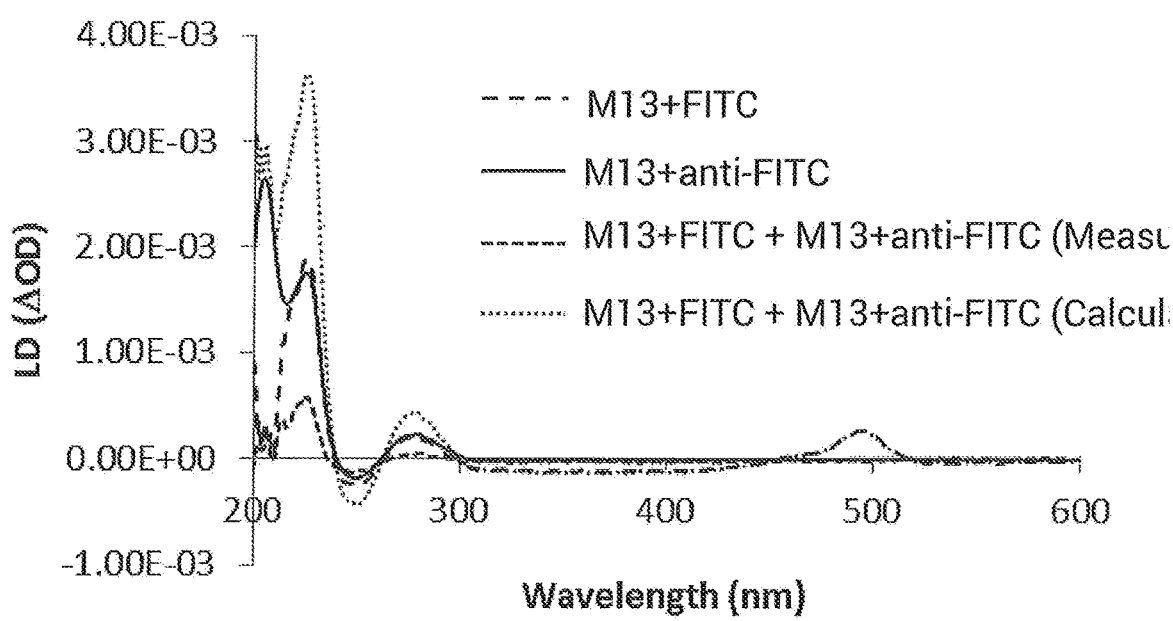

Fluorescein dye absorbs at 494 nm, and FIG. 3 shows that fluorescein labelled M13 produces a fairly large peak at 494 nm, confirming the presence of the dye in solution. The LD signal confirmed that the fluorescein had covalently attached to the M13 as there was a peak at 494 nm in the LD spectrum (FIG. 4). Similar concentrations of M13 conjugated with fluorescein and anti-Fluorescein were used.

When M13 conjugated with anti-fluorescein was added to M13 conjugated with FITC (producing M13-fluorescein), a clear reduction in the LD signal (5.15E-05 ΔOD at 280 nm) was seen in comparison to the LD signals produced by both M13 conjugated with either fluorescein or anti-fluorescein alone (2.11E-04 ΔOD and 2.32E-04 ΔOD at 280 nm respectively) (FIG. 4). The signal produced by the addition of both M13 conjugated with fluorescein and anti-fluorescein was used as a control in this assay. Theoretically this signal should have been twice as large (approximately 4.43E-04 ΔOD at 280 nm) because twice the amount of M13 was present in this sample. However it is thought that the control produces a much lower LD signal because there is cross linking between the M13 bacteriophages, as the fluorescein antigens cross link the anti-fluorescein Abs. This will prevent the M13 bacteriophages from aligning and thus causes a drop in LD signal.

Figure 5:
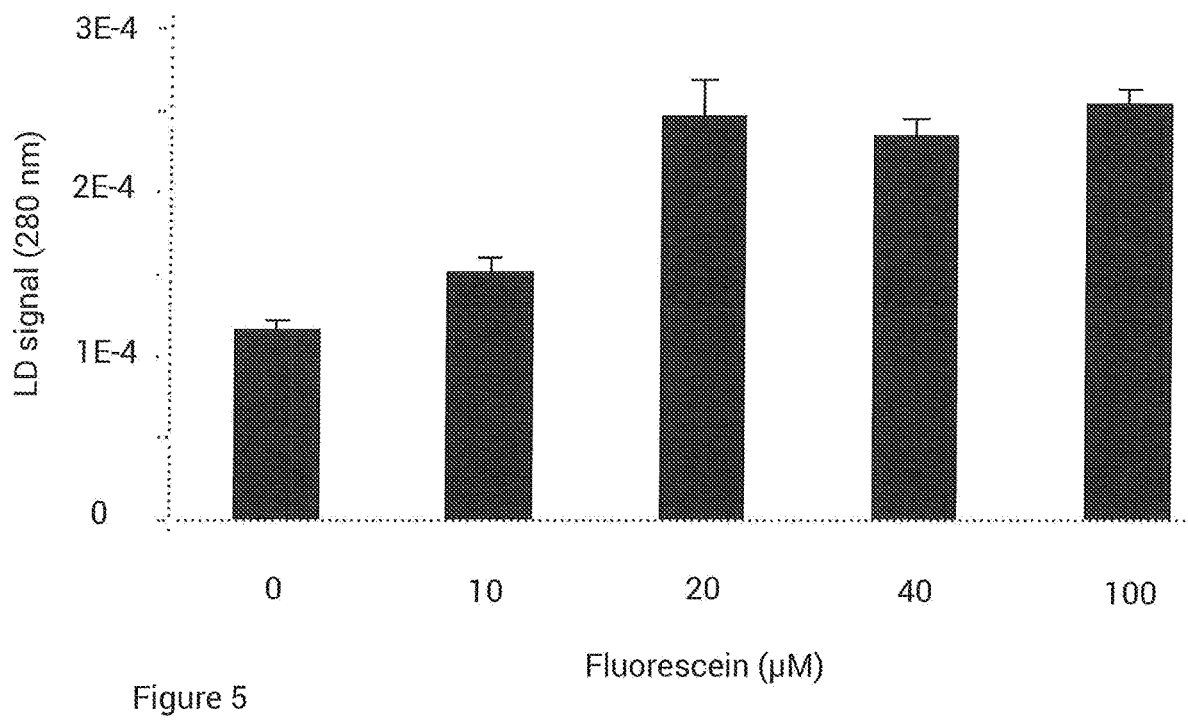

The experiment containing both M13 conjugates revealed a large drop in LD signal compared to that expected if the LD signals from each of the individual reagents were summed (as would be expected if they did not interact). These data suggest that the two conjugates interact with one another (via the fluorescein-antifluorescein interaction) forming a complex that shows reduced alignment. These reagents were then used to detect free fluorescein by adding increasing concentrations of free fluorescein to M13 conjugated with anti-Fluorescein; the formation of a complex between the fluorescein and the M13-anti-Fluorescein serving to block future interactions with the M13-Fluorescein. To determine the sensitivity of this assay, concentrations of fluorescein ranging from 0.01 mM to 2 mM were pre-incubated with M13 anti-Fluorescein prior to the addition of M13-Fluorescein. These results show that this assay was able to detect the fluorescein by showing an increase in LD signal (FIG. 5). The results show that the M13-fluorescein:M13-antifluorescein complex produces a fairly small LD signal of 1.17E-04 ΔOD at 280 nm. When 0.01 mM of fluorescein is added to M13 conjugated with anti-fluorescein and competed with M13 conjugated with fluorescein the signal increases to 1.53E-04 ΔOD at 280 nm. The LD signal then significantly increased to 2.48E-04 ΔOD at 280 nm when 0.02 mM of fluorescein was added to the assay. Further increasing the fluorescein concentrations to 0.04 mM, 0.1 mM, 0.2 mM, 0.5 mM and 1 mM produced similar LD signals to that of 0.02 mM, this (FIG. 5). Overall the results indicate that this assay is sensitive enough to detect 0.01 mM fluorescein.

Detection of Trinitrotoluene (TNT) Using LD and Anti-TNT and TNBS Labelled M13

In a similar way to the detection of fluorescein detailed above, the reagents required for the detection of TNT in this assay included M13 conjugated with anti-TNT and M13 conjugated with the TNT analogue TNBS (2,4,6-trinitrobenzenesulfonic acid). The UV/Vis absorbance spectrum was measured to determine the concentration.

When the LD signal of M13 conjugated to anti-TNT and M13 conjugated with the TNT analogue TNBS are measured separately they result in a certain value represented in the first two bars of FIG. 6. When they are mixed together the LD signal is reduced (third bar from left in FIG. 6) because there is cross linking between the M13 bacteriophages, as the TNBS antigens bind to the anti-TNT antibodies. This will prevent the M13 bacteriophages from aligning and thus causes a drop in LD signal. However, when the mixing is carried out in the presence of TNT, the reduction in signal is smaller (fourth bar from left in FIG. 6).

The invention claimed is:

1. A method for detecting the presence of a target molecule in a sample, comprising the steps of:
   providing an alignable scaffold comprising a first binding region and having a high aspect ratio of greater than 5:1;
   providing a substrate comprising a second binding region which binds the first binding region in the absence of the target molecule in such a way that a linear dichroism (LD) signal of the alignable scaffold is reduced or minimised relative to the unbound and aligned scaffold, wherein one of the first and second binding regions is a receptor capable of binding the target molecule;
   exposing the substrate-bound scaffold to the sample such that binding of the target molecule, if present, to the receptor releases the scaffold from the substrate; and
   measuring the LD signal of the scaffold before and after exposure to the sample.

2. The method of claim 1, wherein the receptor is the first binding region.

3. The method of claim 2, comprising an initial step of attaching the receptor to the scaffold to form a receptor/scaffold complex.

4. The method of claim 1, wherein the receptor is the second binding region.

5. The method of claim 4 comprising an initial step of attaching the receptor to the substrate.

6. The method of claim 1, wherein the LD signal is measured by inducing alignment of the scaffold in solution.

7. The method of claim 6, wherein the substrate comprises a surface within a reaction vessel observable by the LD spectrometer with one or more ligands attached to the surface which bind to the first binding region of the scaffold, thereby sequestering the scaffold to the surface in a non-alignable form.

8. The method of claim 6, wherein, the substrate comprises a surface within a reaction vessel not observable by the LD spectrometer release of the scaffold in the presence of free target molecules allowing the alignable scaffold to move into range of the LD spectrometer thereby allowing an LD signal to be recorded.

9. The method of claim 6, wherein alignment of the scaffold in solution is induced by providing a flow path.

10. The method of claim 1, wherein the scaffold moiety is selected from synthetic and natural polymers, carbon nanotubes and biomolecular fibres.

11. The method of claim 10, wherein the biomolecular fibre is a lipid vesicle, filamentous bacteriophage, amino acid polymer or a nucleic acid polymer.

12. The method of claim 1, wherein the first binding region is a receptor for the target molecule and the substrate comprises one or more second binding regions which comprises at least a portion of the target molecule.

13. The method of claim 12, wherein the second binding region is in the form of a ligand attached to the substrate by covalent interactions.

14. The method of claim 1, wherein an increase in the LD signal detected is proportional to the concentration of the target molecules in the sample, the free target molecules and relevant binding region binding to the receptor via non-covalent interactions, so that competition for the receptor between the target molecules and the relevant binding region creates a chemical equilibrium.

15. The method of claim 1, wherein the substrate binds the scaffold such that the scaffold is in a non-aligned form thereby minimising or reducing the LD signal of the scaffold.

16. The method of claim 1, wherein the substrate comprises a non-alignable moiety (NAM).

17. The method of claim 1, wherein the substrate comprises or consist of an alignable moiety which is only rendered unalignable by virtue of it being bound to the scaffold.

18. The method of claim 17, wherein the scaffold-bound moiety and substrate are the same.

* * * * *